(12) United States Patent
Lin et al.

(10) Patent No.: US 7,408,022 B2
(45) Date of Patent: Aug. 5, 2008

(54) COMPOSITION AND METHOD FOR INCREASING APOPTOSIS IN CANCER CELLS

(75) Inventors: Yao-Zhong Lin, Nashville, TN (US); Claudia Budu, Nashville, TN (US)

(73) Assignee: Celtek Bioscience, LLC, Nashville, TN (US)

( * ) Notice: Subject to any disclaimer, the term of this patent is extended or adjusted under 35 U.S.C. 154(b) by 17 days.

(21) Appl. No.: 11/270,295

(22) Filed: Nov. 9, 2005

(65) Prior Publication Data

US 2006/0099275 A1   May 11, 2006

Related U.S. Application Data

(60) Provisional application No. 60/626,163, filed on Nov. 9, 2004.

(51) Int. Cl.
    *C07K 5/10* (2006.01)
(52) U.S. Cl. ..................................... 530/300
(58) Field of Classification Search .............. None
    See application file for complete search history.

(56) References Cited

U.S. PATENT DOCUMENTS

2002/0169121 A1   11/2002   Ronai
2003/0095979 A1   5/2003    Mattner et al.

OTHER PUBLICATIONS

Freshney, Culture of Animal Cells, A Manual of Basic Technique, Alan R. Liss, Inc., 1983, New York.*
Dermer, Bio/Technology, 1994, 12:320.*
Zips, In Vivo, 2005, 19:1-7.*
Gura, Science, 1997, 278:1041-1042.*
Jain, Sci. Am., 1994, 271:58-65.*
Curti, Crit. Rev. in Oncology/Hematology, 1993, 14:29-39.*
Lin et al., Inhibition of Nuclear Translocation of Transcription Factor NF-kB by a Synthetic Peptide Containing a Cell Membrane-permeable Motif and Nuclear Localization Sequence, *J. Biol. Chem.*, Jun. 1995, vol. 270, No. 24, pp. 14255-14258.
Sumitomo, M. et al., An Essential Role for Nuclear Factor Kappa B in preventing TNF-α-induced Cell Death in Prostate Cancer Cells, *J. Urol.*, Feb. 1999, vol. 161, pp. 674-679.
Poulaki, V. et al., Constitutive Nuclear Factor- κB Activity is Crucial for Human Retinoblastoma Cell Viability, Am. J. Pathol., Dec. 2002, vol. 161, No. 6, pp. 2229-2240.
Garg, A. and Aggarwal, BB., Nuclear Transcription Factor κ-B as a Target for Cancer Drug Development, *Leukemia*, 2002, vol. 16, pp. 1053-1068.
Baldwin, A.S., Control of Oncogenesis and Cancer Therapy Resistance by the Transcription Factor NF-κB, *J. Clin. Invest.*, Feb. 2001, vol. 207, No. 3, pp. 241-246.
Yamamoto, Y. and Gaynor, R., Therapeutic Potential of Inhibition of the NF- κB Pathway in the Treatment of Inflammation and Cancer, *J. Clin Invest.*, Jan. 2001, vol. 107, No. 2, pp. 135-142.
Mitsiades, N., Biologic Sequelae of Nuclear Factor- κB Blockade in Multiple Myeloma: Therapeutic Applications, *Blood*, Jun. 1, 2002, vol. 99, No. 11, pp. 4079-4086.
Hawiger, J., Noninvasive Intracellular Delivery of Functional Peptides and Proteins, *Curr. Opin. Chem. Biol.*, 1999, vol. 3, pp. 89-94.
Shukla, S. and Gupta, S., Suppression of Constitutive and Tumor Necrosis Factor α-Induced Nuclear Factor (NF)- κB Activation and Induction of Apoptosis by Apigenin in Human Prostate Carcinoma PC-3 Cells: Correlation with Down-Regulation of NF- κB-Responsive Genes, *Clin. Cancer Res.*, May 1, 2004, vol. 10, pp. 3169-3178.
Duffey, D., et al., Expression of a Dominant-Negative Mutant Inhibitor- κBα of Nuclear Factor- κB in Human Head and Neck Squamous Cell Carcinoma Inhibits Survival, Proinflammatory Cytokine Expression, and Tumor Growth in Vivo, *Cancer Res.*, Jul. 15, 1999, vol. 59, pp. 3468-3474.

* cited by examiner

*Primary Examiner*—Misook Yu
*Assistant Examiner*—Mark Halvorson
(74) *Attorney, Agent, or Firm*—Donna Russell

(57) ABSTRACT

The invention provides cell permeable peptides and peptide agents that inhibit anti-apoptotic processes in cancer cells to promote tumor cell death, as well as a method for providing therapeutic treatment for cancer. The composition may be delivered in conjunction with a conventional chemotherapeutic agent to provide a synergistic effect that significantly increases the effectiveness of the chemotherapeutic agent to destroy cancer cells. The invention also provides kits or systems for cancer therapy, comprising at least one peptide agent for inhibiting the anti-apoptotic effects of NF-kB and at least one chemotherapeutic agent for stimulating the cellular apoptotic pathway.

3 Claims, 16 Drawing Sheets

Fig. 1

CB5005 Peptide:     <u>KLKLALALALA</u>VQRKRQKLMP

CB5003 Peptide:           <u>LALALA</u>VQRKRQKLMP

CB5002 Peptide:           LALLAPVQRKRQKLMP

CB5007 Peptide:     <u>KLKLALALALA</u>VQRNGQKLMP

Cisplatin

Cisplatin + CB5005

Cisplatin

Cisplatin + CB5003

Cisplatin + CB5002

Cisplatin + CB5007

SEQUENCE LISTING

<160> NUMBER OF SEQ ID NOS: 6

<210> SEQ ID NO 1
<211> LENGTH: 6
<212> TYPE: PRT
<213> ORGANISM: Artificial
<220> FEATURE:
<223> OTHER INFORMATION: Synthesized peptide
<220> FEATURE:
<221> NAME/KEY: Peptide
<222> LOCATION: (1)..(6)

<400> SEQUENCE: 1

Leu Ala Leu Ala Leu Ala
1               5

<210> SEQ ID NO 2
<211> LENGTH: 11
<212> TYPE: PRT
<213> ORGANISM: Artificial
<220> FEATURE:
<223> OTHER INFORMATION: Synthesized peptide
<220> FEATURE:

```
<221> NAME/KEY: Peptide
<222> LOCATION: (1)..(11)

<400> SEQUENCE: 2

Lys Leu Lys Leu Ala Leu Ala Leu Ala Leu Ala
1               5                   10

<210> SEQ ID NO 3
<211> LENGTH: 16
<212> TYPE: PRT
<213> ORGANISM: Artificial
<220> FEATURE:
<223> OTHER INFORMATION: Synthesized peptide
<220> FEATURE:
<221> NAME/KEY: Peptide
<222> LOCATION: (1)..(16)

<400> SEQUENCE: 3

Leu Ala Leu Ala Leu Ala Val Gln Arg Lys Arg Gln Lys Leu Met Pro
1               5                   10                  15

<210> SEQ ID NO 4
<211> LENGTH: 21
<212> TYPE: PRT
<213> ORGANISM: Artificial
<220> FEATURE:
<223> OTHER INFORMATION: Synthesized peptide
<220> FEATURE:
<221> NAME/KEY: Peptide
<222> LOCATION: (1)..(21)

<400> SEQUENCE: 4

Lys Leu Lys Leu Ala Leu Ala Leu Ala Leu Ala Val Gln Arg Lys Arg
1               5                   10                  15

Gln Lys Leu Met Pro
            20

<210> SEQ ID NO 5
<211> LENGTH: 16
<212> TYPE: PRT
<213> ORGANISM: Artificial
<220> FEATURE:
<223> OTHER INFORMATION: Synthesized peptide
<220> FEATURE:
<221> NAME/KEY: Peptide
<222> LOCATION: (1)..(16)

<400> SEQUENCE: 5

Leu Ala Leu Leu Ala Pro Val Gln Arg Lys Arg Gln Lys Leu Met Pro
1               5                   10                  15

<210> SEQ ID NO 6
<211> LENGTH: 21
<212> TYPE: PRT
<213> ORGANISM: Artificial
<220> FEATURE:
<223> OTHER INFORMATION: Synthesized peptide
<220> FEATURE:
<221> NAME/KEY: PEPTIDE
<222> LOCATION: (1)..(21)

<400> SEQUENCE: 6

Lys Leu Lys Leu Ala Leu Ala Leu Ala Leu Ala Val Gln Arg Asn Gly
1               5                   10                  15

Gln Lys Leu Met Pro
            20
```

COMPOSITION AND METHOD FOR INCREASING APOPTOSIS IN CANCER CELLS

CROSS-REFERENCE TO RELATED APPLICATIONS

This application claims the benefit of priority of U.S. patent application Ser. No. 60/626,163 filed Nov. 9, 2004.

STATEMENT IN REGARD TO GOVERNMENT RIGHTS

This invention was made in part with funding provided by the United States Government (Grant number CA99340, awarded by the National Institutes of Health, National Cancer Institute). The U.S. Government may therefore have certain rights in this invention.

FIELD OF THE INVENTION

The present invention relates to cell permeable peptides and the use of those peptides to carry functional cargo through tissues and into cells. The invention also relates to factors that inhibit NF-kB activation.

BACKGROUND OF THE INVENTION

Prostate cancer (PCA) is the second leading cause of cancer-related deaths in the United States. Androgen ablation is often used as therapy because it stimulates apoptosis in androgen-dependent prostate cancer cells. PCA cells are often androgen-independent, and some become androgen-independent over time. Androgen-independent cells are eventually selected during androgen ablation therapy and progression to an androgen-independent state is the primary cause of mortality in men with prostate cancer. Androgen-independent tumor cells are more difficult to destroy, having been shown to be insensitive to many anti-cancer drugs and tumor necrosis factor-alpha (TNF-alpha) therapy. Androgen-independent PCA cells are responsive to high doses of chemotherapeutic drugs such as cisplatin and etoposide, but the drugs themselves have an undesirable level of systemic toxicity. Providing levels high enough to affect a significant number of tumor cells may pose an unacceptable risk to the patient.

Androgen-independent prostate cancer cells (e.g., PC-3 and DU145) have proven to be TNF-α insensitive, whereas androgen-sensitive prostate cancer cells (e.g., LNCaP) are TNF-α sensitive. Resistance to the pro-apoptotic effects of TNF-α and many known chemotherapeutic agents has been associated with constitutive activation of NF-kB in many cancer cells. Muenchen, et al., (*Clin. Cancer Res.* 2000, 6: 1969-1977) demonstrated that inhibition of NF-kB with the IκBα "super-repressor" (p6R-I κB$_{S32A+S36A}$) could sensitize previously insensitive prostate cancer cells to the effects of TNF-α. In most cell types, NF-kB is constitutively present in the cytosol in a latent, inactive form where it is retained through interaction with IkB proteins, which bind to NF-kB and mask its nuclear localization sequence (NLS). In some cell types, NF-kB is constitutively activated. Activation of NF-kB in the cell involves ubiquitination of IkB so that it is degraded by the 26S proteasome. Removal of IkB exposes the NLS and results in translocation of NF-kB to the nucleus, where it acts to protect the cell from apoptosis.

Constitutive activation of NF-kB has been reported in a variety of tissues, including, for example, breast, pancreas, liver, bladder, lung, kidney, and ovary. Neuroblastoma, Hodgkin's lymphoma, acute lymphoblastic leukemia, acute myelogenous leukemia, chronic lymphocytic leukemia, Burkitt's lymphoma, and multiple myeloma are among the cancers associated with constitutive activation of NF-kB. Inhibition of NF-kB nuclear translocation has also been demonstrated to have some effect in sensitizing multiple myeloma to the pro-apoptotic effects of doxorubicin (Mitsiades, et al., *Blood*, (June 2002) 99: 4079-4086). NF-kB activation has therefore become a target for improving cancer therapy.

It is preferable to utilize target-specific agents for cancer therapy and to develop agents that increase the destruction of cancer cells without similarly affecting normal cells. What are especially needed are new agents for those cancers that have shown resistance to current modes of therapy and therefore have an increased mortality rate.

SUMMARY OF THE INVENTION

The present invention relates to polypeptides comprising a cell-permeable peptide of about 6 to about 50 residues comprising at least six consecutive residues of SEQ ID NO: 1 and an NF-kB nuclear localization sequence. The invention also relates to polypeptides comprising a cell-permeable peptide of about 11 to about 50 residues comprising at least eleven consecutive residues of SEQ ID NO: 2 and an NF-kB nuclear localization sequence. The nuclear localization sequence (NLS) of NF-kB can comprise for example, p50, p65, or their functional equivalents. The invention also provides a method for inhibiting NF-κB nuclear translocation in a cell comprising administering to the cell an effective amount of a peptide comprising SEQ ID NO: 3, SEQ ID NO: 4, or a combination thereof. The method may be used therapeutically for a variety of disease states or metabolic abnormalities in which NF-kB nuclear translocation and constitutive activation of NF-kB, particularly, plays a significant role.

The invention also provides a cell permeable peptide of about 6 to about 50 amino acids comprising SEQ ID NO: 1 and a cell permeable peptide of about 11 to about 50 amino acids comprising SEQ ID NO: 2. The cell permeable peptide can be synthesized, produced in a cellular or cell-free DNA or RNA expression system, or chemically attached so that it is functionally associated with a cargo molecule. The cargo molecule may be a modulator of internal cellular activity, an inducer of cell-cell signaling, a hormone, an oligonucleotide, or other active agent, for example.

The invention also provides a chemotherapy system for cancers associated with constitutive NF-kB activation, the system comprising therapeutically effective amounts of a peptide comprising SEQ ID NO: 3, SEQ ID NO: 4, or a combination thereof, and a chemotherapeutic or adiotherapeutic agent that induces apoptosis in a tumor cell. The chemotherapeutic agent can comprise, for example, TNFα, etoposide or cisplatin. The invention also provides a method for treating androgen-independent prostate cancer comprising administering to a subject in need thereof a therapeutically effective amount of at least one peptide that inhibits constitutive activation of NF-kB in a cancer cell in conjunction with a chemotherapeutic agent. The at least one peptide can comprise, for example, SEQ ID NO: 3, SEQ ID NO: 4, SN50, or a combination thereof.

BRIEF DESCRIPTION OF THE DRAWINGS

FIG. 1 illustrates the design and the amino acid sequence of CB5005 (single-letter amino acid code) (SEQ ID NO: 4), a peptide agent that inhibits NF-κB activation, induces apoptosis of human prostate cancer cells, and sensitizes tumor cells to the tumoricidal effects of anti-cancer drugs such as cisplatin and etoposide. CB5005 (SEQ ID NO: 4) contains the nuclear localization sequence (NLS) of the NF-κB p50 protein (in italics) as well as a novel 11-mer cell-penetrating sequence (CPS) (SEQ ID NO: 2) (underlined). CB5003 (SEQ ID NO: 3) is an analogous peptide possessing only a portion of the CPS (also underlined). CB5002 (SEQ ID NO: 5) contains a mutated CPS and thus is not cell-permeable and functional. CB5007 (SEQ ID NO: 6) is a control peptide corresponding to CB5005 except that two basic residues in the NF-kB p50 NLS are mutated (KR-NG).

FIG. 7b illustrates a histogram view of the results in FIG. 7a.

FIG. 1b illustrates cytotoxicity study of different cell lines treated with CB5005 (SEQ ID NO: 4). DU145, PC3, LNCaP, or N2a cells grown in 96-well plates were treated with different concentrations of peptide in quadruplicates for 24 h at 37° C. The cytotoxicity was determined using MTS colorimetric assay (Promega) for 1 h and read at 490 nm using a Bio-Tek Microplate Autoreader EL 309. The data were expressed as mean ±SEM of three independent experiments. Statistical significance (p<0.05) was observed between peptide-untreated and treated samples (30 μM) in DU145 and PC3 cells, but not in LNCaP and N2a cells.

DETAILED DESCRIPTION

Figure 2:
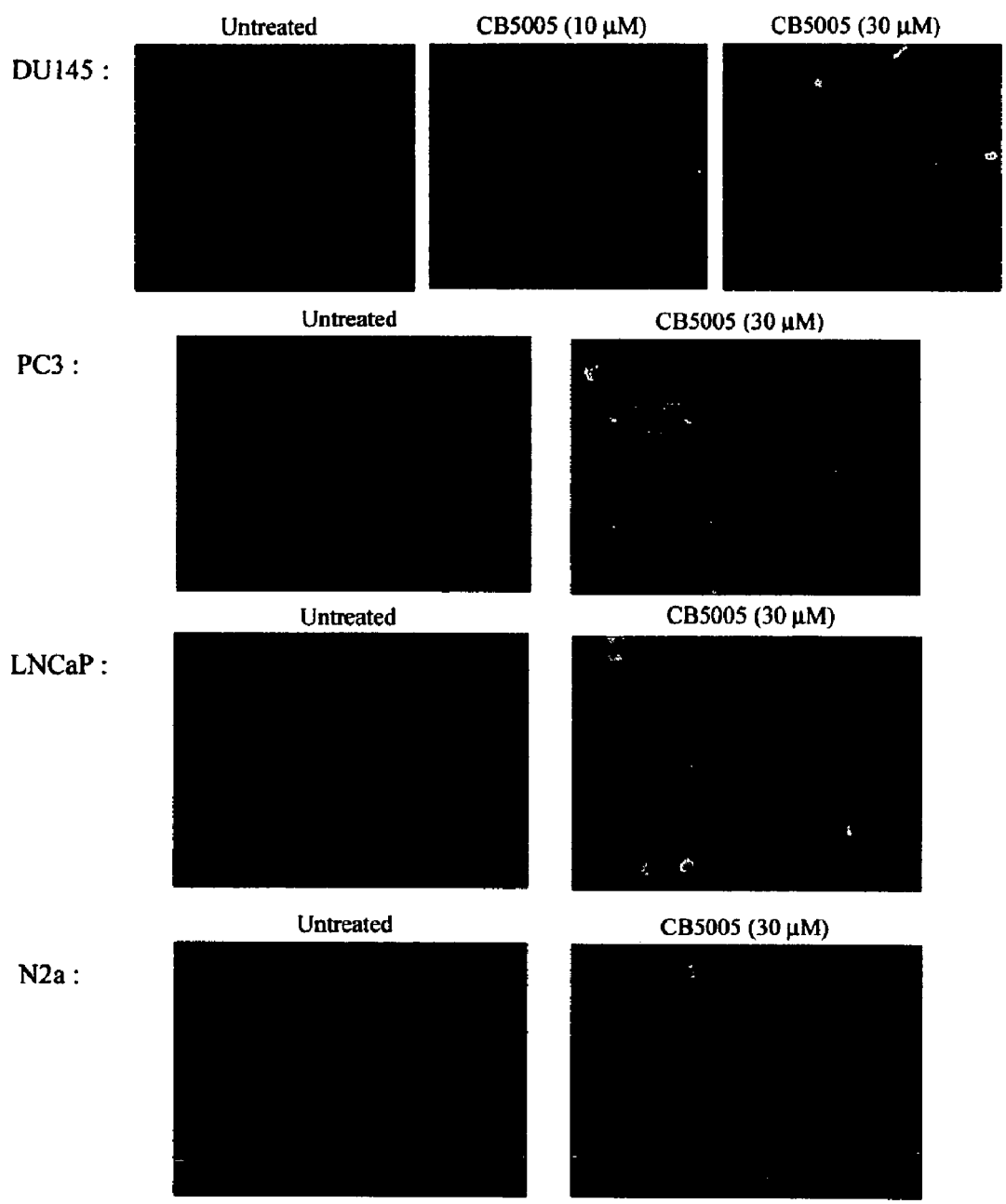
FIG. 2 illustrates cellular import of CB5005 (SEQ ID NO: 4) in DU145, PC3, LNCaP, and N2a cells by fluorescence microscopy analysis. Cells on 8-well chamber slides were treated at 37° C. for 1 hour with 30 μM CB5005 (SEQ ID NO: 4). Intracellular peptide was detected using indirect immunofluorescence assay using anti-peptide antibody and FITC-labeled anti-rabbit antibody and analyzed by fluorescence microscopy.

The inventors have designed a novel cell permeable peptide (CPS) that can be functionally attached to an inhibitor of NF-kB activation or nuclear localization to destroy androgen-independent prostate tumor cells (cancer cells). When delivered to a cell, and carrying a cargo peptide that comprises an inhibitor of NF-kB activation, this CPS provides increased inhibition of NF-kB activation over that provided by known inhibitors of NF-kB activation such as SN50. The invention provides peptides that can be administered to inhibit the anti-apoptotic effects of NF-κB either alone, or in conjunction with a chemotherapeutic agent to increase the destruction of tumor cells.

The invention also provides methods of use for novel peptides which induce apoptosis of cancer cells and sensitize tumor cells to the cytocidal effects of chemotherapeutic drugs such as cisplatin and etoposide. Such peptides can inhibit the anti-apoptotic mechanism in a cell, or promote apoptosis in a cell, and generally can comprise peptides of about 6 to about 50 amino acids which include SEQ ID NO: 1 (Leu-Ala-Leu-Ala-Leu-Ala), SEQ ID NO: 2 (Lys-Leu-Lys-Leu-Ala-Leu-Ala-Leu-Ala-Leu-Ala), SEQ ID NO: 3, SEQ ID NO: 4, or combinations thereof. The invention provides novel therapeutic agents for the treatment of androgen-insensitive prostate cancer, as well as a variety of cancer types in which constitutive NF-kB activation induces cellular resistance to apoptosis or inhibits apoptosis.

Peptides of the present invention and peptides used in the method of the present invention can be prepared by standard peptide synthesis methods known to those of skill in the art. Peptides may also be produced using an expression vector having a nucleotide sequence encoding the peptide(s) of choice operably linked to appropriate promoter, terminator, and other functional sequences, such as a sequence encoding a purification tag, to facilitate expression and purification of the peptides. "Operably" or "functionally" linked means that the CPS and its cargo peptide are connected so that the CPS can direct import of the CPS/cargo peptide (e.g., CPS/NLS) into the cell and the cargo peptide can function to affect cellular metabolism, such as cell signaling. A CPS and cargo peptide can be linked, for example, by one or more peptide bonds. The CPS can be immediately C-terminal or N-terminal to the cargo peptide, more than one CPS can be used, more than one cargo peptide can be used, and/or the CPS and cargo peptide amino acid sequences can be separated by one or more amino acids in the region between the CPS and cargo peptide. The CPS/cargo peptide can comprise additional amino acids either C-terminal or N-terminal, or both.

"Chemotherapeutic" agents, as used herein, are chemical agents that stimulate apoptosis in cells, generally (but not always) having a greater effect on cancer or tumor cells than on normal cells. A variety of chemotherapeutic agents are known to those of skill in the art. Agents known to those of skill in the art of cancer therapy to stimulate apoptosis of cancer cells also include radiotherapeutic agents. Peptides of the present invention can also be used to augment the effects of radiotherapeutic agents and to provide a synergistic effect to promote the destruction of cancer cells.

Cell permeable, "importation competent" signal peptide sequences, and membrane translocation sequences facilitate the transport of attached peptides and proteins into cells. Several sequences of this kind have previously been described, including the hydrophobic region of the signal sequence of Kaposi fibroblast growth factor which has been fused to the nuclear localization sequence (NLS) of p50 to produce the peptide known as SN50 (U.S. Pat. No. 5,807,746). The inventors provide here a novel sequence designed by the inventors to confer improved cell permeability upon an attached peptide or protein. Operably linking NF-kB p50 or a functional counterpart to a cell permeable sequence (CPS) described herein produces a peptide having improved activity when compared to the activity of SN50 under similar conditions of administration. The inventors have demonstrated that a sequence comprising Lys-Leu-Lys-Leu-Ala-Leu-Ala-Leu-Ala-Leu-Ala (SEQ ID No. 2) is even more effective at facilitating cellular import of the p50 NLS than is one of the most widely used cell-permeable inhibitors of NF-kB activation, SN50. The CPS/p50 NLS (SEQ ID NO: 3) peptide produced by the inventors provides effective cell killing of androgen-independent prostate cancer cells when administered in combination with chemotherapeutic agents that trigger the apoptotic pathway in those cells. The CPS/p50 NLS (SEQ ID NO: 4) peptide not only provides a synergistic pro-apoptotic effect when administered with at least one chemotherapeutic or radiotherapeutic agent, but also provides a pro-apoptotic and therapeutic effect when administered without the chemotherapeutic or radiotherapeutic agent.

As used herein, the term "CPS" includes variants or biologically active fragments of the peptides, as well as peptides which may contain additional amino acids either N-terminal or C-terminal (or both) to the disclosed sequences, their derivatives, variants, or functional counterparts. A "functional counterpart" can include, for example, a peptide nucleic acid (PNA). A "variant" of the peptide is not completely identical to a disclosed CPS peptide sequence. A variant, given the disclosure of the present invention, can be obtained by altering the amino acid sequence by insertion, deletion or substitution of one or more amino acid. The amino acid sequence of a disclosed peptide can be modified, for example, by substitution to create a peptide having substantially the same or improved qualities. The substitution may be a conserved substitution. A "conserved substitution" is a substitution of an amino acid with another amino acid having a side chain that is similar in polar/nonpolar nature, charge, or size. The 20 essential amino acids can be grouped as those having nonpolar side chains (alanine, valine, leucine, isoleucine, proline, phenylalanine, and tryptophan), uncharged polar side chains (methionine; glycine, serine, threonine, cysteine, tyrosine, asparagine and glutamine), acidic side chains (aspartate and glutamate) and basic side chains (lysine, arginine, and histidine). Conserved substitutions might include, for example, Asp to Glu, Asn or Gln; His to Lys, Arg or Phe; Asn to Gln, Asp or Glu, Leu to Ile or Val, and Ser to Cys, Thr or Gly. Alanine is commonly used to make conserved substitutions.

To those of skill in the art, variant peptides can be obtained by substituting a first amino acid for a second amino acid at one or more positions in the peptide structure in order to affect biological activity. Amino acid substitutions may, for example, induce conformational changes in a polypeptide that result in increased biological activity.

Those of skill in the art may also make substitutions in the amino acid sequence based on the hydrophilicity index or hydropathic index of the amino acids.

A variant peptide of the present invention has less than 100%, but at least about 50%, and more preferably at least about 80% to about 90% amino acid sequence homology or identity to the amino acid sequence of a corresponding native nucleic acid molecule or polypeptide comprising SEQ ID NO 1, SEQ ID NO 2, SEQ ID NO 3, or SEQ ID NO 4. The amino acid sequence of a variant CPS peptide therefore corresponds essentially to the disclosed amino acid sequences. As used herein, "corresponds essentially to" refers to a polypeptide sequence that will elicit a similar biological activity as that generated by a disclosed CPS, such activity being from at least about 70 percent of that of disclosed CPS peptide, to greater than 100 percent of the activity of a disclosed CPS peptide.

A variant of a disclosed CPS may include amino acid residues not present in the corresponding CPS, or may include deletions relative to the corresponding CPS. A variant may also be a truncated "fragment" as compared to the corresponding CPS, i.e., only a portion of the amino acid sequence of certain disclosed CPSs.

Nuclear factor kappa B (NF-κB) is constitutively activated in androgen-insensitive PCA cells, with activation augmented by TNF-α release in the tissues. NF-κB and the genes it regulates appear to be responsible for induction of anti-apoptosis in human PCA cells. NF-κB nuclear translocation can be inhibited by administration of a CPS/p50 NLS (SEQ ID NO: 3, SEQ ID NO: 4, or a combination thereof) peptide of the present invention to interfere with the NF-κB-regulated anti-apoptotic mechanism. When administered in conjunction with a chemotherapeutic agent that stimulates apoptosis, the CPS/p50 NLS (SEQ ID NO: 3) peptide of the present invention blocks NF-κB activation and subsequent inhibition of apoptosis and facilitates tumor cell killing. When administered either alone or in conjunction with a chemotherapeutic agent that induces apoptosis, the CPS/NLS described by SEQ ID NO: 4 also blocks NF-kB inhibition of apoptosis and facilitates destruction of tumor cells.

The peptide comprising SEQ ID NO: 4 can be administered alone, absent any chemotherapeutic agent, to provide a therapeutic effect. "Alone" is meant to denote that the peptide is provided as the primary therapeutic agent without an additional agent having a significant pro-apoptotic therapeutic effect. It is to be understood that peptides of the present invention or peptides used in the method of the invention can be provided with appropriate pharmaceutical agents known to those of skill in the art, such as, for example, excipients, diluents, solvents, saline solutions, and agents having other desirable therapeutic effects, such as antibiotics and pain relief agents.

The cell permeable sequences of the present invention (SEQ ID NO: 1 and SEQ ID NO: 2), can also be used to deliver a variety of other peptides, nucleic acids, and other organic compounds for research or therapeutic use. Other peptides that can be delivered to the interior of the cell using the method of the present invention include, but are not limited to, peptides that comprise enzyme cleavage sites, phosphorylation sites, protein-protein interaction regions, and receptor binding sites of intracellular proteins. The CPS can also be used to deliver peptides that comprise functional regions of proteins that act within the interior of a cell to promote growth, differentiation, or other cellular functions.

A CPS/p50 NLS of the present invention can also be used in a variety of other therapies including inhibition of nuclear localization of NF-κB for the purpose of decreasing inflammation or pain. NF-kB inhibition has been proposed as a target for therapeutic intervention in rheumatoid arthritis (RA), for example. In rheumatoid arthritis, the synovium becomes an aggressive, tumor-like structure (pannus), and impaired regulation of apoptosis is generally thought to be a causative factor. In an animal model of RA, intraarticular administration of NF-kB decoys prevented the recurrence of streptococcal cell wall-induced arthritis in treated joints, as well as in contralateral, untreated joints. Spinal NF-kB activation has been shown to induce COX-2 upregulation and to induce inflammatory pain hypersensitivity. Inflammatory pain hypersensitivity plays a role in acute and chronic pain states. A CPS/p50 NLS of the present invention can be provided to a site of injury, surgery, trauma, or inflammation to decrease COX-2 upregulation and pain hypersentivity. Peptides can be injected into the intraarticular space or may be provided via catheter from a pump reservoir, the pump being located either within or outside the body. Sustained or modified release compositions can be provided via injection or pump, or may be incorporated into a matrix for implantation at or near the inflammatory site.

Inhibition of NF-kB has also been reported to have a protective effective on transplanted tissues or cells, such as pancreatic islet cells. Peptides of the present invention having a CPS/p50 NLS sequence provided in conjunction with transplant tissues or cells can therefore provide a means to promote cell survival.

Inhibition of NF-kB activation by overexpression of IkBα or truncated p65 has been shown to reduce the inflammatory response and protect an organ from injury in xenotransplantation. Inhibition of NF-kB activation has also been proposed to be effective in preventing tissue damage associated with ischemia/reperfusion, heart attack, and stroke.

The invention is also directed to a method of suppressing induced and/or constitutive activation of NF-κB transcription factor family proteins in cells, such as PCA cells for example, by a polypeptide comprising a CPS functionally linked to a NLS as described above. The method of the present invention provides a means of introducing NF-κB p50 NLS into the interior of human prostate cancer cells for inhibition of nuclear translocation and activation of endogenous NF-κB. The method comprises the step of administering a therapeutically effective amount of a peptide comprising an NF-kB nuclear localization sequence or a functional portion thereof operably linked to a peptide that facilitates transport of the NF-kB nuclear localization sequence into the interior of a cell to a patient in conjunction with a therapeutically effective amount of at least one chemotherapeutic agent. A peptide comprising an NF-kB nuclear localization sequence and a peptide that facilitates transport of the NF-kB NLS into the interior of a cell can comprise, for example, SEQ ID NO: 3, SEQ ID NO: 4, or combinations thereof. A peptide that facilitates transport of the NF-kB nuclear localization sequence into the interior of a cell can comprise, for example, SEQ ID NO: 1, SEQ ID NO: 2, or combinations thereof. The CPS/NF-kB NLS peptide(s) can be administered prior to, concurrent with, or subsequent to administration of the at least one chemotherapeutic agent, and the timing of administration can be dependent upon the route of administration chosen.

A CPS/p50 NLS NF-κB inhibitor, or a peptide comprising a CPS as described by the present invention functionally linked to an inhibitor of NF-kB nuclear localization, such as CB5003 (SEQ ID NO: 3) can also be utilized in cancer cells possessing a similar anti-apoptotic mechanism. In the present invention, the inventors have shown that co-treatment of PCA cells with CB5005 (SEQ ID NO: 4) greatly reduces the concentration of cisplatin or etoposide necessary to induce apoptosis of human PCA cells and dramatically increases efficacy of the chemotherapeutic agent. Furthermore, when used as a chemotherapeutic agent in its own right, in the absence of additional chemotherapeutic agents, CB5005 (SEQ ID NO: 4) can also induce apoptosis in tumor cells.

The invention therefore also provides chemotherapeutic kits or systems comprising therapeutically effective amounts of at least one peptide agent that inhibits the anti-apoptotic action of NF-κB to promote tumor cell destruction or a combination of agents, including at least one peptide agent supplied with at least one chemotherapeutic agent that would trigger the apoptotic pathway in a tumor cell. These can be provided in admixed form or in separate aliquots. In one embodiment, such a kit or system would comprise a CPS/p50 NLS or similar peptide such as, for example, SEQ ID NO: 3, SEQ ID NO: 4, of a combination thereof and at least one chemotherapeutic agent. Chemotherapeutic agents can comprise, for example, TNF-α, cisplatin, etoposide, or other agents that stimulate apoptosis when administered to a patient in need of chemotherapy, particularly in patients diagnosed with androgen-independent prostate cancer. CPS/p50 NLS peptides can comprise the amino acid sequence of SEQ ID NO: 1 or SEQ ID NO: 2, for example, or a variety of sequences which confer membrane permeability upon a peptide operably linked thereto. Such sequences can also include, for example, the signal sequence of Kaposi fibroblast growth factor or a membrane-translocating sequence as described in U.S. Pat. No. 6,780,843.

Therapeutically effective amounts of a peptide agent as provided by the present invention can be determined by those of skill in the art, given the disclosure contained herein, and may vary according to common factors used to determine dosage levels, such as age and weight, as well as according to the tumor size, tumor number, and tumor location in a particular individual for whom the combination of peptide agent and chemotherapeutic agent is prescribed. Administration can be performed by standard routes, such as intravenous administration, intraperitoneal administration, implantation of a sustained-release matrix, device, or composition, or other means known to those of skill in the art.

Sustained release, modified release, or controlled release compositions or devices have been described previously, and may provide administration of a peptide agent as described by the present invention. An interbody pump, for example, may be used to administer the peptide agent, as well as a chemotherapeutic agent administered in conjunction with the peptide agent. An external pump may also be used, particularly when such a pump is operably connected to a catheter for delivery of a peptide agent to a patient's circulatory system or to a target site in patient tissue. Transdermal delivery may also be used for tumors that are located at or near the surface of the skin. Intravenous administration of peptides described herein, or peptides used in the method described herein, may be used. Peptide compositions may be injected using a standard needle/syringe. Injection can be provided, for example, either subcutaneously, intraperitoneally, or intramuscularly.

The increased membrane permeability of a CPS of the present invention also provides a more effective agent for delivering an active agent, comprising, for example, a peptide, protein, DNA, RNA, antisense oligonucleotide, ribozyme, or combination thereof, through one or more tissues to aid in drug delivery. Use of a membrane translocating peptide to provide a drug delivery system has been described in U.S. Pat. No. 6,780,846 (Elan Corporation, PLC). Pharmaceutical compositions such as peptides, proteins, hormones, analgesics, chelating agents, modulators of intracellular metabolism, modulators of cell-cell signaling, etc., can be provided by attaching to a CPS of the present invention. Attachment can be achieved by synthesizing a CPS/active agent cargo combination molecule, by chemically attaching a cargo molecule to an CPS, by producing a CPS/active agent cargo combination molecule in a cellular or cell-free recombinant DNA expression system, or by other means known to those of skill in the art. CPS/active agent molecules can be combined with or delivered by a variety of agents previously described in the art, such as, for example, nanoparticles, nanospheres, liposomes, microspheres, capsules, emulsions and/or micelles. Vaccines, which often comprise peptide or DNA sequences of target organisms, hormones such as insulin, growth hormone, estradiol, and testosterone, for example, chemotherapeutic agents, anti-hypertensives, and other active agents can be delivered by a drug delivery system comprising a CPS of the present invention. Delivery routes can comprise intravenous, intraperitoneal, oral, nasal (by drop or inhalation, for example), topical, or other means known to those of skill in the art. Compositions comprising CPS/active agent molecules of the present invention can be, for example, topically administered to aid in therapy of skin cancers, skin disorders, burns, and chronic wounds.

The invention will be further described by means of the following non-limiting examples.

EXAMPLES

Design and Synthesis of CPS Functional Peptides

Peptides were synthesized by conventional solid-phase peptide synthesis methodology (Celtek Bioscience, Nashville, Tenn.). Standard synthesis protocols based on Fmoc chemistry were used. After synthesis, the crude peptides were cleaved from the solid support and purified by $C_{18}$ reverse-phase HPLC. The purified peptides were characterized by analytical HPLC analysis and mass spectrometry analysis.

For biological assays, peptide stocks were made either in PBS (2 mg/ml) or in DMSO (30 mg/ml) as diluent. The final concentration of DMSO in the culture medium did not exceed 0.1%.

A nuclear localization sequence (NLS) of NF-KappaB p50 protein was used as the functional cargo and a cell-penetrating sequence (CPS) as the carrier. The CPS/NLS synthetic polypeptide was synthesized so that the CPS was located N-terminal to the NLS (FIG. 1). For polypeptide CB5003 (SEQ ID NO: 3), with SEQ ID NO: 1 comprising the CPS. For polypeptide CB5005 (SEQ ID NO: 4), with SEQ ID NO: 2 comprising the CPS. CB5002 (SEQ ID NO: 5) contained a mutant, non-functional CPS located N-terminal to the NLS. CB5007 (SEQ ID NO: 6) contained a mutant, non-functional NLS C-terminal to the CPS.

Cell Lines

Human prostatic adenocarcinoma DU145 and LNCaP cell lines were obtained from American Type Culture Collection (ATCC, Rockville, Md.). Human prostatic adenocarcinoma PC3 cell line was kindly provided by Dr. Lawrence Jones at Huntington Medical Research Institutes, Pasadena, Calif. All three cell lines were maintained in RPMI 1640 supplemented with 10% Fetal Bovine serum, 50 units/ml penicillin, 50 µg/ml streptomycin, and 1 mM sodium pyruvate. For LNCaP cells, 10 mM HEPES and 4.5 g/L glucose were also supplemented. The N2a neuroblastoma cell line was kindly provided by Dr. Yuan Luo, University of Southern Mississippi, Hattiesburg, Miss. USA. N2a cells were maintained in 50% DMEM/50% Opti-MEM supplemented with 5% Fetal Bovine serum. The cell lines were grown in humidified atmosphere at 37° C. with 5% $CO_2$.

Indirect Immunofluorescence Assay for Detecting Peptide Cellular Import

DU145 cells were grown on 8-well chamber slides (Nunc, Naperville, Ill.) to a confluence of 80%. These cells were then incubated with diluent or different concentrations of peptides in RPMI without serum for 1 h at 37° C. The cells were washed three times with cold PBS to remove the extracellular peptides and then fixed with 3.5% paraformaldehyde solution in PBS at 4° C. for 20 min. The fixed cells were washed three times with cold PBS and treated with 0.25% Triton X-100 for 10 min. The washed cells were then incubated with anti-peptide IgG in PBS for 1 h. After three 5 min washings with PBS, the intracellular peptides (via peptide-antibody complexes) were subsequently detected with FITC-labeled goat anti-rabbit IgG (Pierce, Rockford, Ill.) after 1 h incubation. Cover slips with stained cells were mounted in Poly/Mount (Polysciences, Warrington, Pa.) and analyzed with Microstar IV (Reichard, Buffalo, N.Y.) using a 100× oil immersion lens. The color images were analyzed using a Pixera digital camera and stored in JPG format. The same assay was also utilized for determining peptide cellular import in other cell lines, including PC3, LNCaP, and neuroblastoma N2a cells.

Cellular Import of CB5005 (SEQ ID NO: 4) Peptide

The intracellular import activities of CB5005 (SEQ ID NO: 4), CB5003 (SEQ ID NO: 3), CB5002 (SEQ ID NO: 5), and CB5007 (SEQ ID NO: 6) peptides in different cell lines were examined by fluorescence microscopy by analyzing the fluorescent signal in an indirect immunofluorescence assay. As shown in FIG. 2, CB5005 (SEQ ID NO: 4) was cell-permeable to all the cell lines tested, including androgen-independent DU145 and PC3 cancer cells, androgen-dependent LNCaP cancer cells, and neuroblastoma N2a cells.

The cellular import of CB5005 (SEQ ID NO: 4) was also concentration-dependent. However, CB5003 (SEQ ID NO: 3) displayed much weaker import activity, whereas CB5002 was not active in this cellular import assay. CB5007 displayed similar import activity as CB5005 (SEQ ID NO: 4) because these two peptides share the same CPS.

This indirect immunofluoresence assay was also utilized to quantitate peptide cellular import. Briefly, cells grown in 96-well plates will be treated with peptides for different time periods, and then subjected to an indirect immunofluorescence assay using anti-peptide antibody and FITC-labeled anti-rabbit antibody as described above. Cells were then lysed with 10% SDS and the fluorescence in the soluble cell solutions was quantified by a Cytofluor™ 2300 reader (Millipore) at 485/560 nm. The fluorescence readings were calculated by subtracting them from the background reading of peptide-untreated sample. The data were expressed as mean ±SEM of three independent experiments performed in quintuplicate samples. The kinetics of imported CB5005 peptide (SEQ ID NO: 4) was studied by using this quantitative. The time-dependent fluorescence accumulation (628.00±75.60 (1 h), 737.33±37.10 (4 h), and 1,042±58.40 (20 h)) was observed, suggesting a relatively stability of CB5005 peptide (SEQ ID NO: 4) in intracellular compartments, as recognized by the anti-peptide antibodies.

Western Blot Analysis of Nuclear Extract

PCA cells were grown on 60-mm dishes to a confluence of 70-80%. The cells were incubated with different concentrations of peptides for 30 min at 37° C., followed by treatment with TNF-α (10 ng/ml) for an additional 1 h at 37° C., as indicated, or incubated with peptide alone for 16 hours. After the treatment, cells were washed with ice-cold PBS and lysed in 500 µl of buffer A (10 mM HEPES, pH 7.9, 10 mM KCl, 0.1 mM EDTA, 0.1 mM EGTA, 0.4% Nonidet P-40, 1 mM DTT, 0.5 mM PMSF and 1 µg/ml each of leupeptin, aprotinin, pepstatin, chymostatin and antipain) on ice for 10 min. Nuclei were pelleted by centrifugation at high speed and washed with 500 µl of buffer A. Nuclei were then resuspended in 40 µl of buffer B (20 mM HEPES, pH 7.9, 400 mM NaCl, 1 mM EDTA, 1 mM EGTA, 1 mM DTT, 1 mM PMSF and 1 µg/ml each of leupeptin, aprotinin, pepstatin, chymostatin and antipain). The protein concentration of nuclear extract was determined using Pierce BCA protein assay and equalized among samples using buffer B.

Equal amounts of proteins were heat-treated in 2×SDS sample loading buffer at 100° C. for 5 minutes and fractionated by 10% SDS polyacrylamide electrophoresis. The proteins were transferred to nitrocellulose paper. After blocking with 5% nonfat milk in TBS (10 mM Tris-HCl, pH 7.6, 70 mM NaCl and 0.05% Tween 20) for 30 minutes, nuclear NFκB p50 was detected by using an anti-p50 IgG antibody (1:5000), (Upstate, Lake Placid, N.Y.). The primary antibody was visualized with horseradish peroxidase-coupled secondary antibody by using ECL western blotting system as described in manufacturer's protocol (Pierce, Rockford, Ill.).

Figure 3A:
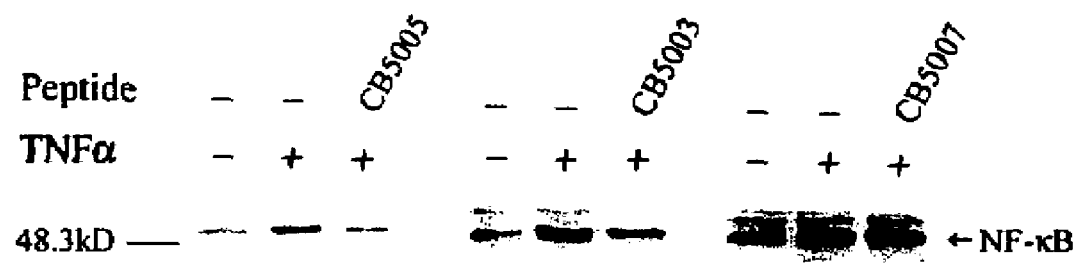
FIG. 3a illustrates Western blot analysis of NF-κB p50 protein in nuclear extracts of androgen-independent DU145 cells. DU145 cells were treated with CB5005 (SEQ ID NO: 4) (30 μM), CB5003 (SEQ ID NO: 3) (90 μM), CB5007 (SEQ ID NO: 6) (30 μM), or diluent for 30 min followed by TNF-α (10 ng/ml) or diluent for an additional 1 h. Equal quantities of nuclear extract were separated by SDS-PAGE and proteins were transferred to a nitrocellulose membrane. NF-κB p50 protein was detected using anti-p50 rabbit antibody and enhanced chemiluminescence.
Figure 3B:
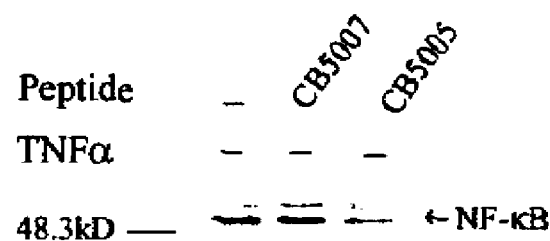
FIG. 3b illustrates Western blot analysis of NF-κB p50 protein in nuclear extracts of androgen-independent DU145 cells. DU145 cells were treated with CB5005 (SEQ ID NO: 4) (30 μM), CB5007 (SEQ ID NO: 6) (30 μM), or diluent for 16 h. No TNF-α was added.

Inhibition of NF-κB Nuclear Translocation and Activation in Human Prostate Cancer Cells DU145 is an androgen-independent prostate cancer cell line that displays constitutive NF-κB activation that can be further enhanced by TNF-α treatment. LNCaP, an androgen-dependent cell line, does not exhibit constitutive NF-κB activation, but NF-κB activation can be stimulated by TNF-α treatment. NF-κB activation usually results in its rapid import into the nucleus. Therefore, Western blot analysis of NF-κB proteins in nuclear extracts was used to assess the extent of NF-κB activation. CB5005 (SEQ ID NO: 4) and CB5003 (SEQ ID NO: 3) functionally linked to the NF-κB p50 NLS inhibited TNF-α-induced NF-κB nuclear translocation in both DU145 (FIG. 3a) and LNCaP cells relative to the control. CB5007 (SEQ ID NO: 6), a control peptide with a mutant NLS, did not have an inhibitory effect in either cell line. CB5005 (SEQ ID NO: 4) also inhibits constitutive activation of NF-kB (FIG. 3b).

The inhibitory effect of these peptides on functional activity of NF-κB in prostate cancer cells was quantified by measuring NF-κB binding to a double-stranded oligonucleotide encoding the κB recognition site by an enzyme-linked immunoassay (ELISA) using specific NF-κB p50 antibodies. The nuclear extract form the peptide-pretreated DU145 cells showed significantly lower NF-κB binding activity relative to peptide-untreated cells, confirming that these peptides inhibited both TNF-α-induced and constitutive NF-κB nuclear translocation in DU145 cells.

Fluorescence Microscopy

DU145 cells were grown on 4-well chamber slides to a confluence of 70-80%. Cells were then treated with CB5005 peptide (SEQ ID NO: 4) (30 µM) or diluent for 30 min at 37°

C. followed by cisplatin (5 μg/ml) for an additional 5 h. After treatment, the cells were washed with binding buffer and resuspended in binding buffer containing Annexin V-FITC and propidium iodide (PI) for 15 min in the dark at room temperature as suggested by manufacturer's protocol (BD Biosciences, San Diego, Calif.). The chamber slides were mounted in Poly/mount (Polysciences, Warrington, Pa.) and analyzed with a fluorescence microscope (Microstar IV, Reichard, Buffalo, N.Y.) using ×100 oil immersion lens. The color images were analyzed by a Pixera digital camera and stored in JPG format.

TUNEL Assay

DU145 cells were grown on 8-well chamber slides to a confluence of 70-80%. The cells were then incubated with different concentrations of peptides or diluent for 30 min at 37° C. followed by the treatment with cisplatin (5 μg/ml) or diluent for an additional 16 h. The cells were air-dried and fixed in 4% paraformaldehyde at room temperature for 1 h. The cells were then washed with PBS and permeabilized with permeabilization solution (0.1% Triton X-100 in 0.1% sodium citrate) for 2 min on ice. Apoptosis was detected using TUNEL method "in situ cell death detection POD" according to the manufacturer's instructions (Roche, Indianapolis, Ind.). The fluorescein-labeled DNA strand breaks due to apoptosis were visualized under light microscope (Microstar IV, Reichard, Buffalo, N.Y.) by using anti-fluorescein antibody conjugated POD (peroxidase) at ×40 magnification. The images were analyzed using a Pixera digital camera.

Flow Cytometric Analysis

PCA cells were grown on 60-mm dishes to a confluence of 50-60%. These cells were incubated with different concentrations of peptides for 30 min at 37° C. followed by the treatment with TNF-α (10 ng/ml), cisplatin (2-30 μg/ml), etoposide (2-20 μg/ml) or diluent for an additional 21 h at 37° C. Phosphatidylserine exposure on apoptotic cells was measured by their ability to bind Annexin V. Specifically, cells were harvested by trypsinization. The trypsinized cells, media and PBS washes were combined and cells collected by centrifugation. The collected cells were washed with binding buffer and resuspended in 70 μl of binding buffer containing Annexin V-FITC and PI for 15 min on dark at room temperature as suggested by manufacturer's protocol (BD Biosciences, San Diego, Calif.). Stained cells were analyzed by flow cytometry. A minimum 20,000 events for each sample was measured.

Effect of CB5005 (SEQ ID NO: 4) Peptide on Induction of Apoptosis of Androgen-Independent PCA Cells and Sensitization and Enhancement of the Killing of These Cancer Cells by Chemotherapeutic Drugs.

Figure 4:
FIG. 4 illustrates apoptotic DU145 cells stained with annexin V/PI. DU145 cells on 4-well chamber slides were treated with CB5005 (SEQ ID NO: 4) (30 μM) or diluent for 30 min followed by cisplatin (5 μg/ml) for an additional 5 h. The cells were then treated with the annexin V/PI kit as instructed by the manufacturer's protocol (BD-Pharmingen) and examined by fluorescent microscopy. The fluorescence-stained cells indicate apoptotic cells.
Figure 4:
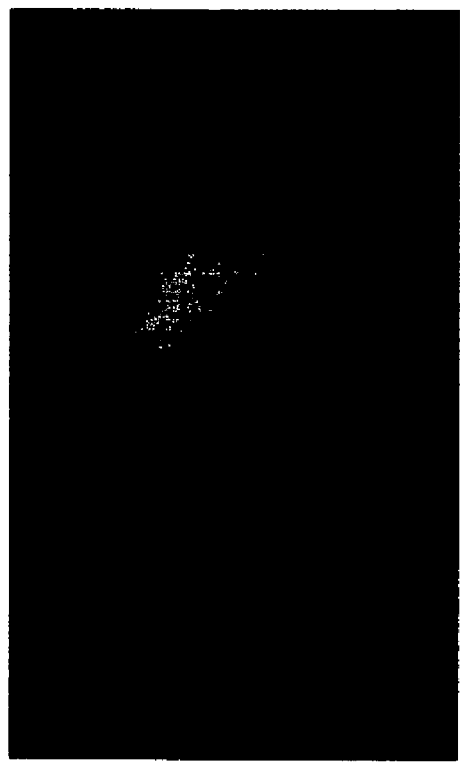
Figure 5:
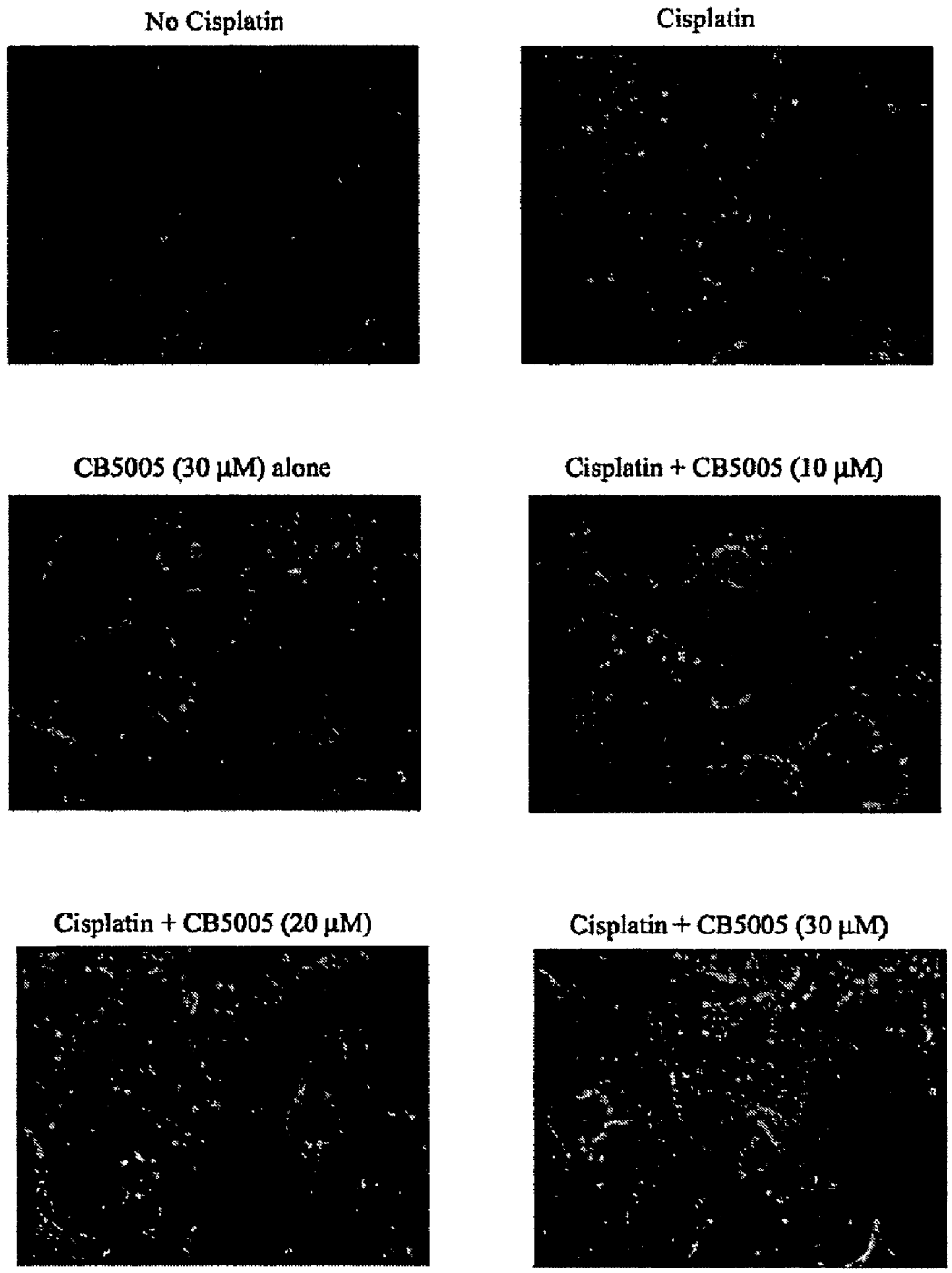
FIG. 5 illustrates apoptotic DU145 cells using the TUNEL reaction kit (Roche), which preferentially labels DNA strand breaks generated during apoptosis. DU145 cells on 8-well chamber slides were treated with CB5005 (SEQ ID NO: 4) at the indicated concentrations or diluent for 30 min followed by cisplatin (5 μg/ml) or diluent for an additional 16 h. Arrows indicate dark brown areas of DNA fragmentation detected in the nuclei, a common sign of apoptosis.
Figure 6:
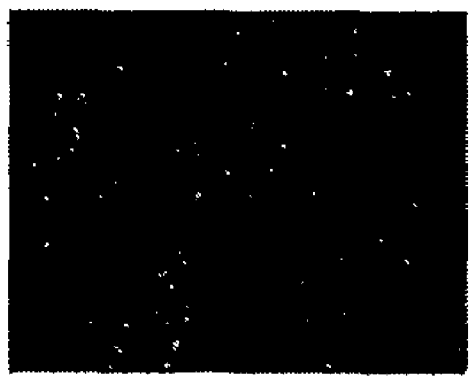
FIG. 6 illustrates apoptotic DU145 cells using the TUNEL reaction kit (Roche), which preferentially labels DNA strand breaks generated during apoptosis. DU145 cells on 8-well chamber slides were treated with CB5003 (SEQ ID NO: 3) (40 μM), CB5002 (SEQ ID NO: 5) (72 μM), CB5007 (SEQ ID NO: 6) (30 μM), or diluent for 30 min followed by cisplatin (5 μg/ml) for an additional 16 h.
Figure 6:
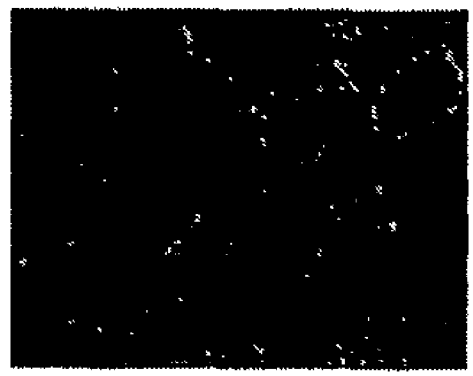
Figure 6:
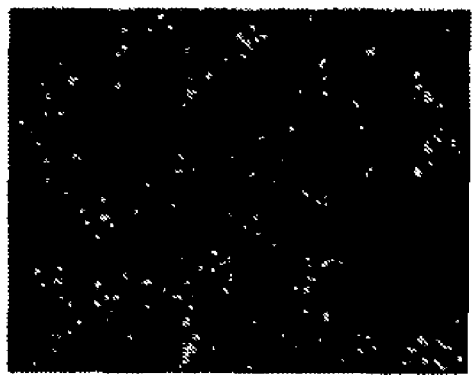
Figure 6:

CB5005 (SEQ ID NO: 4) peptide agent was utilized to treat androgen-independent DU145 cells together with cisplatin. In the absence of CB5005 (SEQ ID NO: 4), cisplatin (5 μg/ml) was ineffective in inducing apoptosis in DU145 cells as determined by an annexin V/PI-based fluorescence microscopy analysis (FIG. 4), in which the early stage of apoptosis can be detected by annexin V-FITC-bound phosphatidylserine (PS) at the outer cell membrane released from the interior of apoptotic cells. However, when DU145 cells were co-treated with CB5005 (SEQ ID NO: 4) peptide and cisplatin, apoptosis was induced as demonstrated by strong annexin V-FITC staining (FIG. 4). This synergistic activity of CB5005 (SEQ ID NO: 4) was confirmed by a different apoptosis assay—TUNEL assay—which preferentially labels DNA strand breaks generated during apoptosis (FIG. 5). This sensitizing activity of CB5005 (SEQ ID NO: 4) was concentration-dependent, reaching maximum at the concentration of 20 μM (FIG. 5). Interestingly, treatment of cells with CB5005 (SEQ ID NO: 4) alone also induced a low level of apoptosis, suggesting that constitutive NF-κB activation is responsible for sustaining the growth of DU145 tumor cells (FIG. 5). CB5003 (SEQ ID NO: 3), but not CB5002 (SEQ ID NO: 5) or CB5007 (SEQ ID NO: 6), was also active, although at a much lower level as compared with CB5005 (SEQ ID NO: 4) (FIG. 6). These results together indicate that CB5005 (SEQ ID NO: 4) is an effective agent capable of sensitizing the androgen-independent prostate cancer DU145 cells to the killing by anticancer drugs.

Figure 7A:
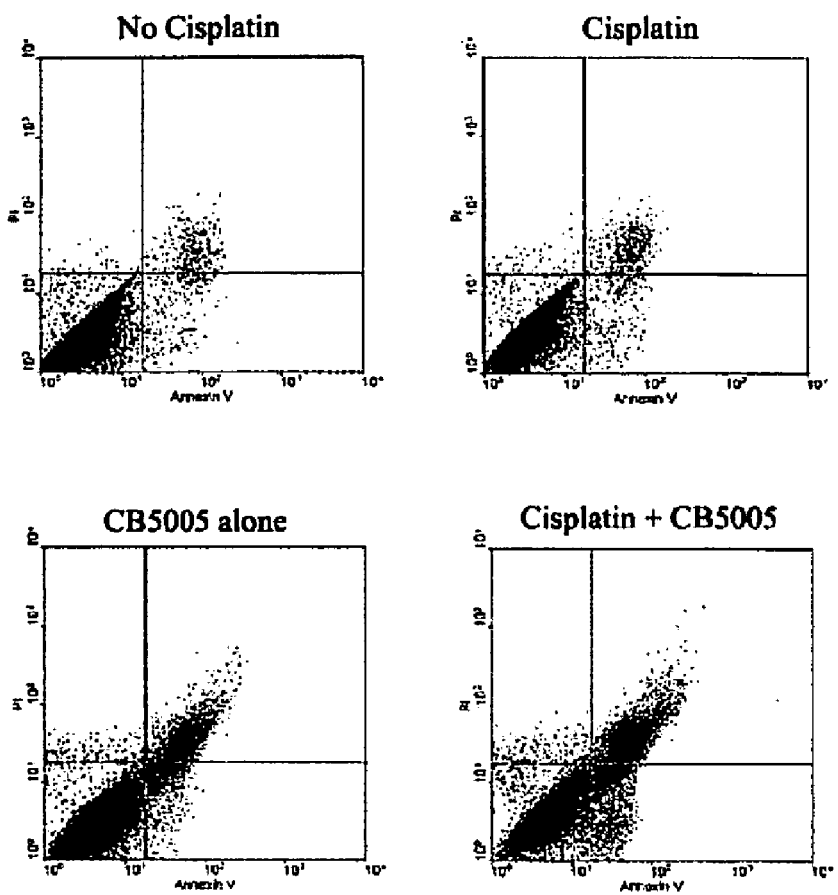
FIG. 7a illustrates flow cytometric analysis of DU145 cells stained with annexin V/PI. DU145 cells were treated with CB5005 (SEQ ID NO: 4) (30 μM) or diluent for 30 min followed by cisplatin (5 μg/ml) or diluent for an additional 21 h. Cells were then analyzed by flow cytometry.
Figure 7B:
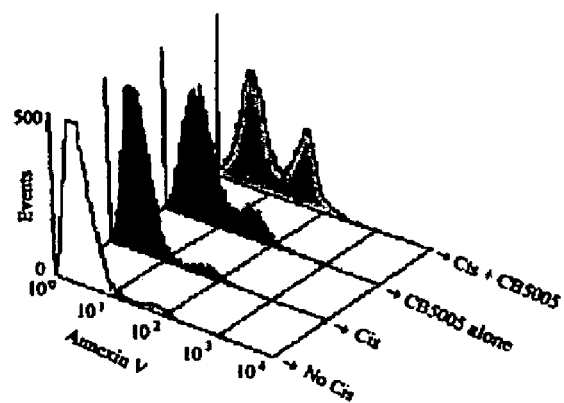
Figure 8:
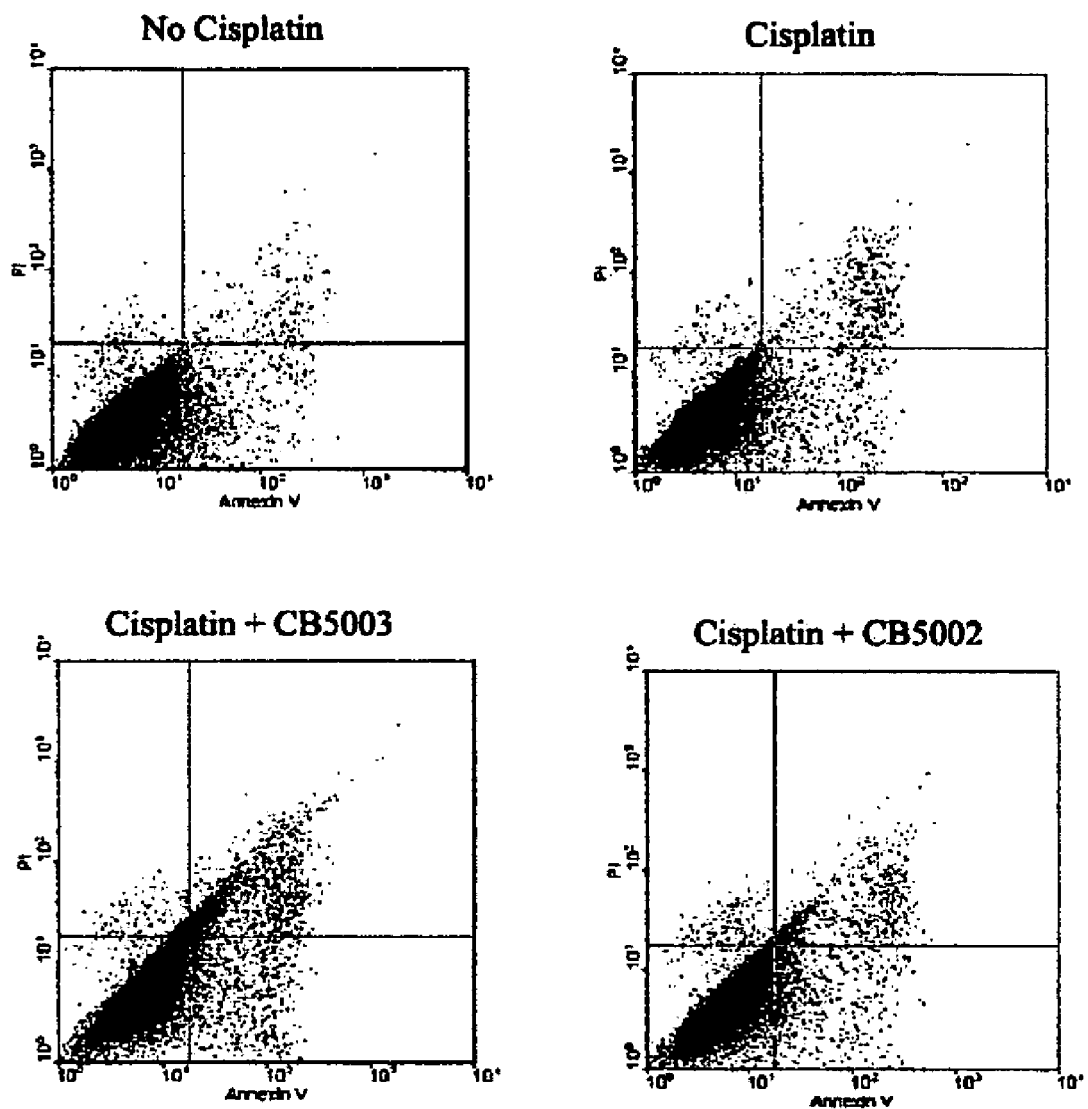
FIG. 8 illustrates flow cytometric analysis of DU145 cells stained with annexin V/PI. DU145 cells were treated with CB5003 (SEQ ID NO: 3) (72 μM), CB5002 (72 μM), or diluent for 15 min followed by cisplatin (5 μg/ml) or diluent for an additional 21 h. The cells were then analyzed by flow cytometry.
Figure 9:
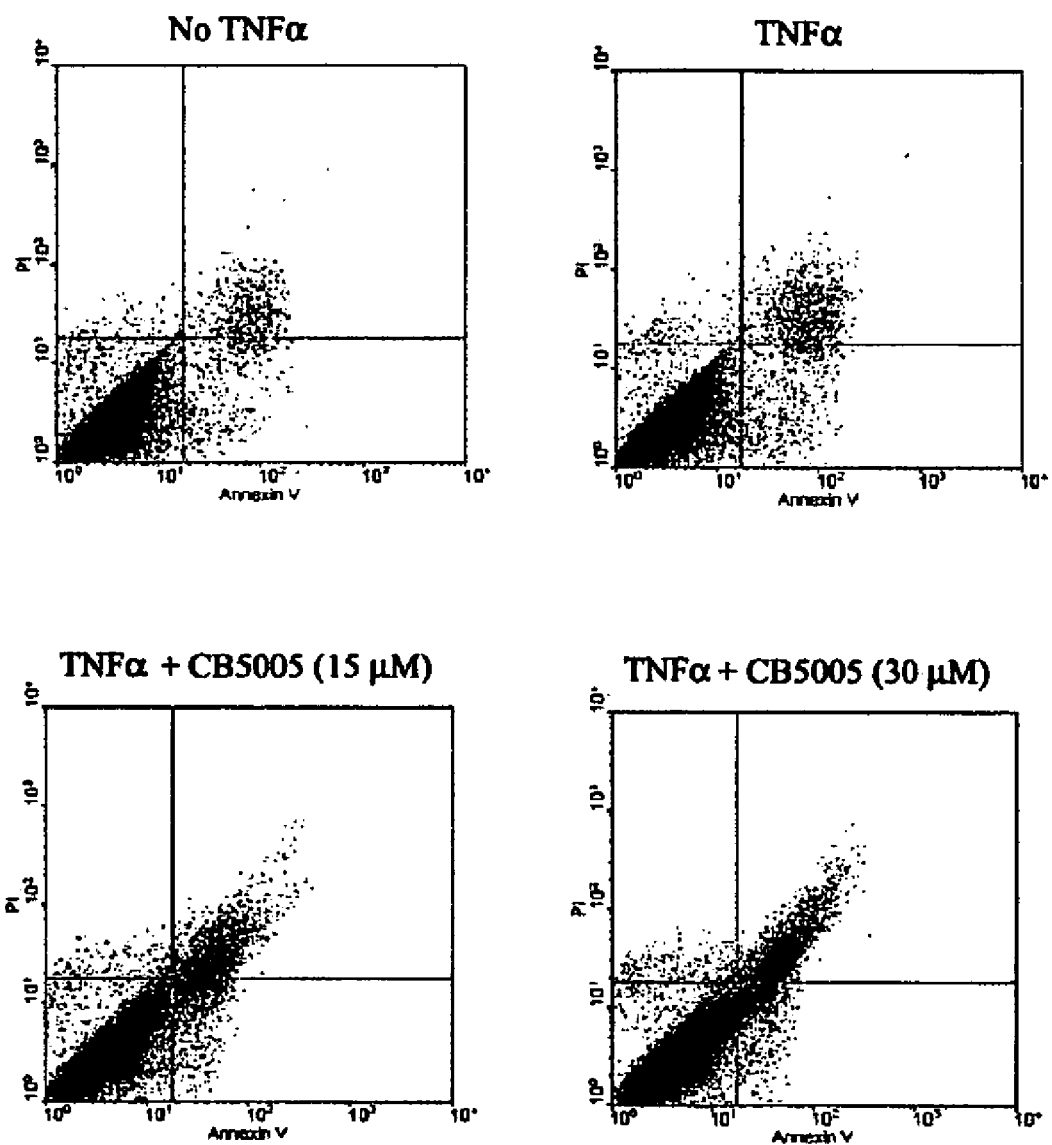
FIG. 9 illustrates flow cytometric analysis of DU145 cells stained with annexin V/PI. DU145 cells were treated with CB5005 (SEQ ID NO: 4) at the indicated concentrations or diluent for 30 min followed by TNF-α (10 ng/ml) or diluent for an additional 21 h. The cells were then analyzed by flow cytometry.

The ability of CB5005 (SEQ ID NO: 4) to sensitize the killing of advanced prostate cancer DU145 cells by cisplatin was quantified by measuring the level of annexin V/PI labeling of the cells by flow cytometry. DU145 cells were treated with cisplatin alone, CB5005 (SEQ ID NO: 4) alone, or co-treated with CB5005 (SEQ ID NO: 4) and cisplatin (FIG. 7). While cisplatin treatment (5 μg/ml) was ineffective and CB5005 (SEQ ID NO: 4) treatment (30 μM) was partially effective, co-treatment of the two agents significantly induced the apoptosis in DU145 cancer cells (FIG. 7). Again, CB5003 (SEQ ID NO: 3) was active but to a much less extent as compared with CB5005 (SEQ ID NO: 4) (FIG. 8). CB5002 (SEQ ID NO: 5), a control peptide for CB5003 (SEQ ID NO: 3), did not show significant effect in these apoptosis-based experiments (FIG. 8). Finally, CB5005 (SEQ ID NO: 4) was also capable of sensitizing the apoptosis in DU145 cells induced by TNFα (FIG. 9).

Figure 10A:
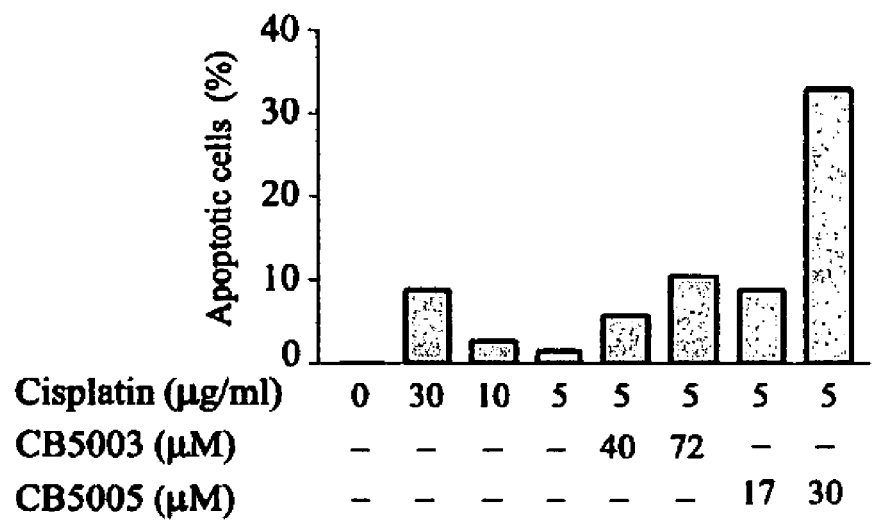
FIG. 10a indicates percentages of the apoptotic cells induced by cisplatin in the absence or presence of CB5005 (SEQ ID NO: 4) or CB5003 (SEQ ID NO: 3) in DU145 cells, as calculated from the results of flow cytometric analysis. The experimental condition was the same as that in FIG. 7.
Figure 10B:
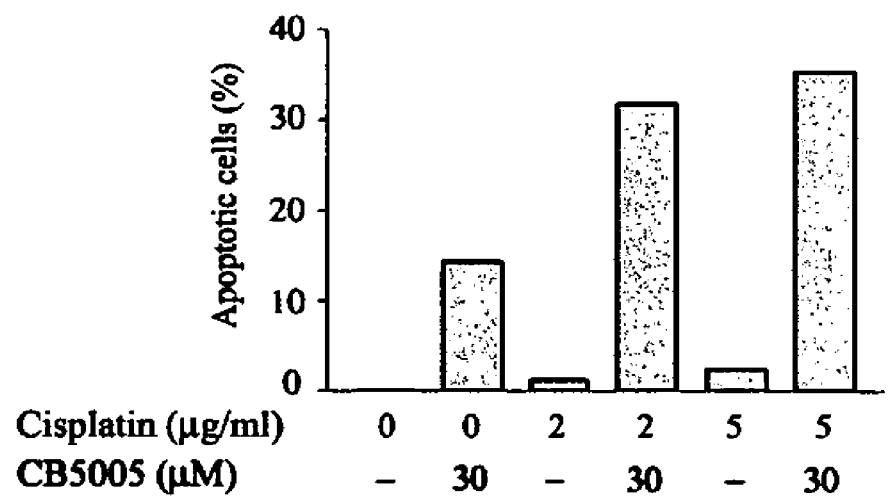
FIG. 10b illustrates and compares the percentages of the apoptotic cells induced by cisplatin alone, CB5005 (SEQ ID NO: 4) alone, and co-treatments of cisplatin and CB5005 (SEQ ID NO: 4) in DU145 cells, as calculated from the results of flow cytometric analysis.

The synergistic activity of CB5005 (SEQ ID NO: 4) or CB5003 (SEQ ID NO: 3) in enhancing the apoptosis induced by cisplatin was concentration-dependent (FIG. 10a). In the case of CB5005 (SEQ ID NO: 4)/cisplatin, co-treatment of CB5005 (SEQ ID NO: 4) at 30 μM stimulated an about 15-fold increase in apoptosis in DU145 cancer cells as compared to those treated with cisplatin alone. This synergistic activity by CB5005 (SEQ ID NO: 4) peptide was not changed greatly when the cisplatin dosage was reduced from 5 μg/ml to 2 μg/ml (FIG. 10b). Interestingly, CB5005 (SEQ ID NO: 4) treatment alone (without cisplatin) was also quite active in stimulating apoptosis of these tumor cells (FIG. 10b).

Figure 11:
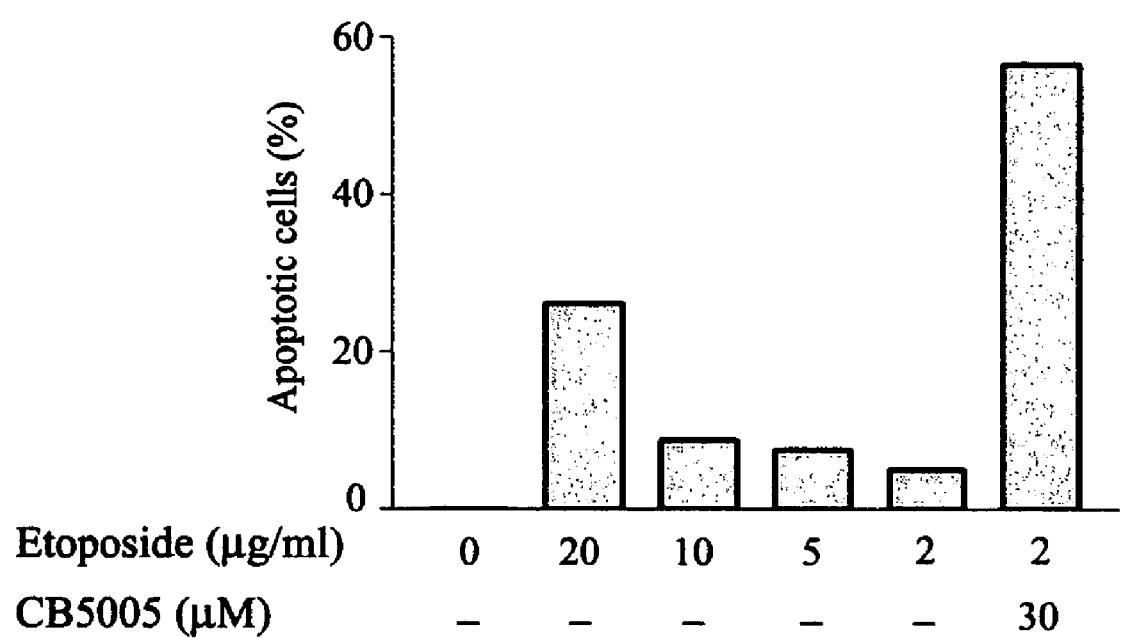
FIG. 11 indicates percentages of the apoptotic cells induced by etoposide in the absence or presence of CB5005 (SEQ ID NO: 4) in DU145 cells, as calculated from the results of flow cytometric analysis. DU145 cells were treated with CB5005 (SEQ ID NO: 4) (30 μM) or diluent for 30 min followed by etoposide at the indicated concentrations for an additional 21 h. The cells stained with annexin V/PI were then analyzed by flow cytometry.

An even greater synergistic activity of CB5005 (SEQ ID NO: 4) was observed with etoposide, another anti-cancer drug to which advanced PCA cells show resistance (FIG. 11). A high percentage of apoptotic cells (nearly 60%) was detected by flow cytometric analysis of DU145 cells co-treated with etoposide (2 μg/ml) and CB5005 (SEQ ID NO: 4) (30 μM) for 21 h (FIG. 11).

Taken together, these experimental data have clearly demonstrated that co-treatment of DU145 cells with CB5005 (SEQ ID NO: 4) and cisplatin or etoposide (2 μg/ml).is much more effective in inducing apoptosis in PCA cells as compared with the treatment using these anticancer drugs alone at a much high dose (20-30 μg/ml).

In Vitro Cytotoxicity Assay

LNCaP, DU145, PC3, or neuroblastoma N2a cells were grown in 96-well plates to a confluence of 60%. The treatments with different concentrations of peptide were performs in quadruplicates in a total volume of 100 μl in RPMI without serum for 24 h at 37° C. The cells were then washed and incubated at 37° C. with 100 μl phenol-red free RPMI containing 20 μl of the CellTiter 96 AQueous Solution reagent (Promega, Madison, Wis.) for 1 h. The absorbency in each well was recorded at 490 nm using a Microplate Autoreader EL 309 (Bio-Tek Instruments, Winooski, Vt.). The absorbency reflects directly the number of viable cells. Blanks were subtracted from all data. The data were then analyzed using Prism software (GraphPad Software Inc., San Diego, Calif.) and expressed as a mean ±SE of three independent experiments. Statistical significance was performed by one way ANOVA and consider significant if $p<0.05$.

Figure 12A:
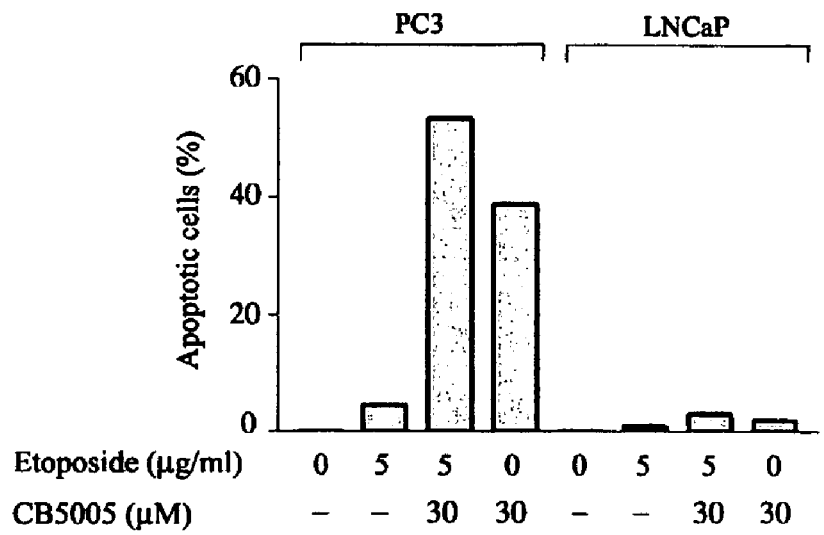
FIG. 12a indicates and compares percentages of the apoptotic cells induced by etoposide in the absence or presence of CB5005 (SEQ ID NO: 4) in PC3 cells and LNCaP cells, as calculated from the results of flow cytometric analysis. PC3 cells or LNCaP cells were treated with CB5005 (SEQ ID NO: 4) (30 μM) or diluent for 30 min followed by etoposide at 5 μg/ml for an additional 21 h. The cells stained with annexin V/PI were then analyzed by flow cytometry.
Figure 12B:
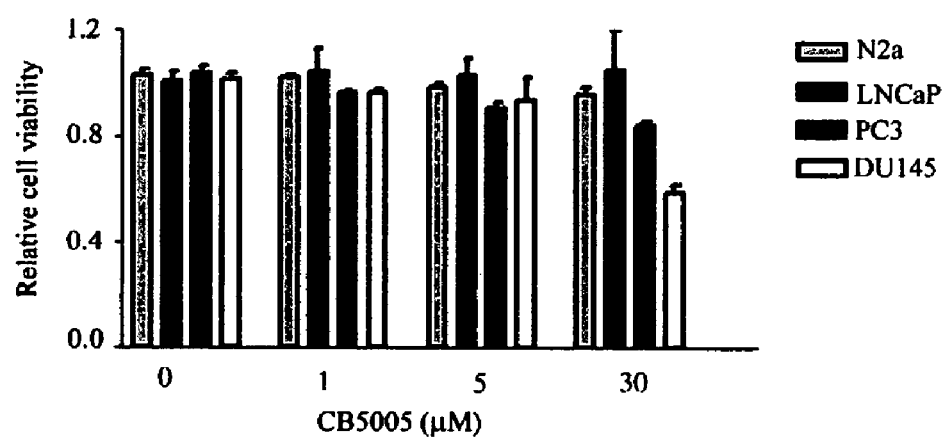

Specificity of CB5005's (SEQ ID NO: 4) Synergistic Activity to Androgen-Independent PCA Cells To determine whether the activity of CB5005 (SEQ ID NO: 4) in inducing apoptosis of PCA cells is specific to androgen-independent cells, the inventors examined the effect of this peptide on androgen-dependent LNCaP cells that do not display constitutive NF-κB activation. As shown in FIG. 12a, CB5005 (SEQ ID NO: 4) sensitized androgen-independent PC3 cells to etoposide-induced apoptosis, but did not sensitize androgen-dependent LNCaP cells to the pro-apoptotic effects of etoposide. Results from a MTS cytotoxic assay also indicated that CB5005 (SEQ ID NO: 4) was not toxic to LNCaP cells (FIG. 12b). Furthermore, the results indicate that CB5005 peptide (SEQ ID NO: 4) treatment did not result in toxicity to neuroblastoma N2a cells (FIG. 12b). Taken together, the results indicate that the pro-apoptotic activity of CB5005 is specific to androgen-independent prostate cancer cells which are characterized by constitutive NF-kB activation.

Spectrofluorimetric Caspase 3 Quantification

PC3 cells were grown on 60-mm dishes to a confluence of 90%. Cells were then incubated with CB5005 (SEQ ID NO: 4) for 30 min at 37° C. followed by the treatment with etoposide (5 µg/ml) or diluent for 16 h. After the treatment, the cells were harvested by trypsinization. The trypsinized cells, media and PBS washes were combined and cells collected by centrifugation. Collected cells were lysed in caspase 3 buffer (20 mM Tris-HCl, pH 7.2, 150 mM NaCl, 1% Triton X-100, 1 mM DTT) on ice for 30 min. Equal amount of proteins were incubated at room temperature with 2× caspase reaction buffer (100 mM HEPES, pH 7.5, 10% sucrose, 0.1% CHAPS, 0.2% BSA with freshly added 10 mM dithiothreitol and 50 µM Asp-Glu-Val-Asp aminomethylcoumarin (DEVD-AMC) as the substrate). Samples were excited at 380 nm and read at 460 nm in a Cytofluor™ 2300 (Millipore, Bedford, Mass.). Relative fluorescence was calculated by subtracting the blank fluorescence (buffer plus substrate only) from the sample fluorescence.

Data are expressed as a mean ±SEM. Statistical significance was performed by student t test for paired data and consider significant if $p<0.05$.

Involvement of Caspase-3 in CB5005-Induced Apoptosis

Figure 13:
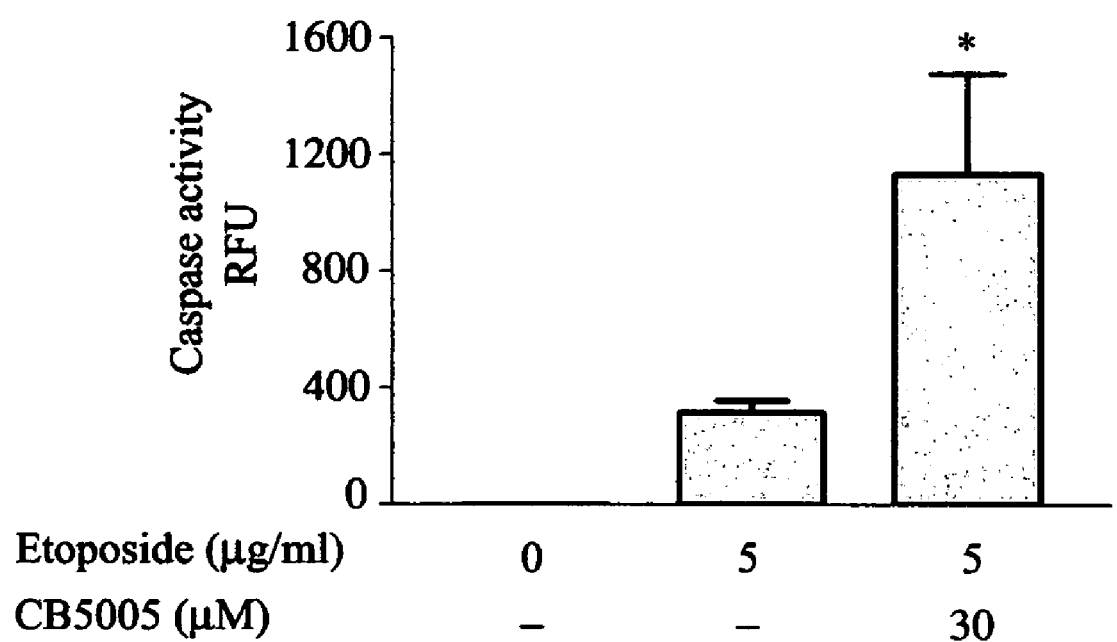
FIG. 13 illustrates the effect of CB5005 (SEQ ID NO: 4) on enhancing caspase-3 activity in PC3 cells induced by etoposide. PC3 cells were treated with CB5005 (SEQ ID NO: 4) (30 μM) or diluent for 30 min followed by etoposide at 5 μg/ml for an additional 16 h. The caspase-3 activity in cell lysates was measured by spectrofluorimetric caspase-3 quantification assay kit using Asp-Glu-Val-Asp aminomethylcoumarin (DEVD-AMC) as a substrate. Samples were excited at 380 nm and read at 460 nm in a Cytofluor™ 2300 reader (Millipore, Bedford, Mass.). Relative fluorescence was calculated by subtracting the blank fluorescence (buffer plus substrate only) from the sample fluorescence. Results are expressed as the mean of three different experiments ±SEM. (* indicates that values are significantly different (p<0.05) from the cells treated with etoposide alone).

Caspase-3 activity was elevated in PC3 cells when treated with both CB5005 (SEQ ID NO: 4) and etoposode (FIG. 13), indicating that the pro-apoptotic effect of CB5005 (SEQ ID NO: 4) in PCA cells involves the action of effector caspase-3.

CB5005 (SEQ ID NO:4) is more potent than SN50 in terms of enhancing the apoptosis of PCA cells induced by cytotoxic drug agents.

Figure 14:
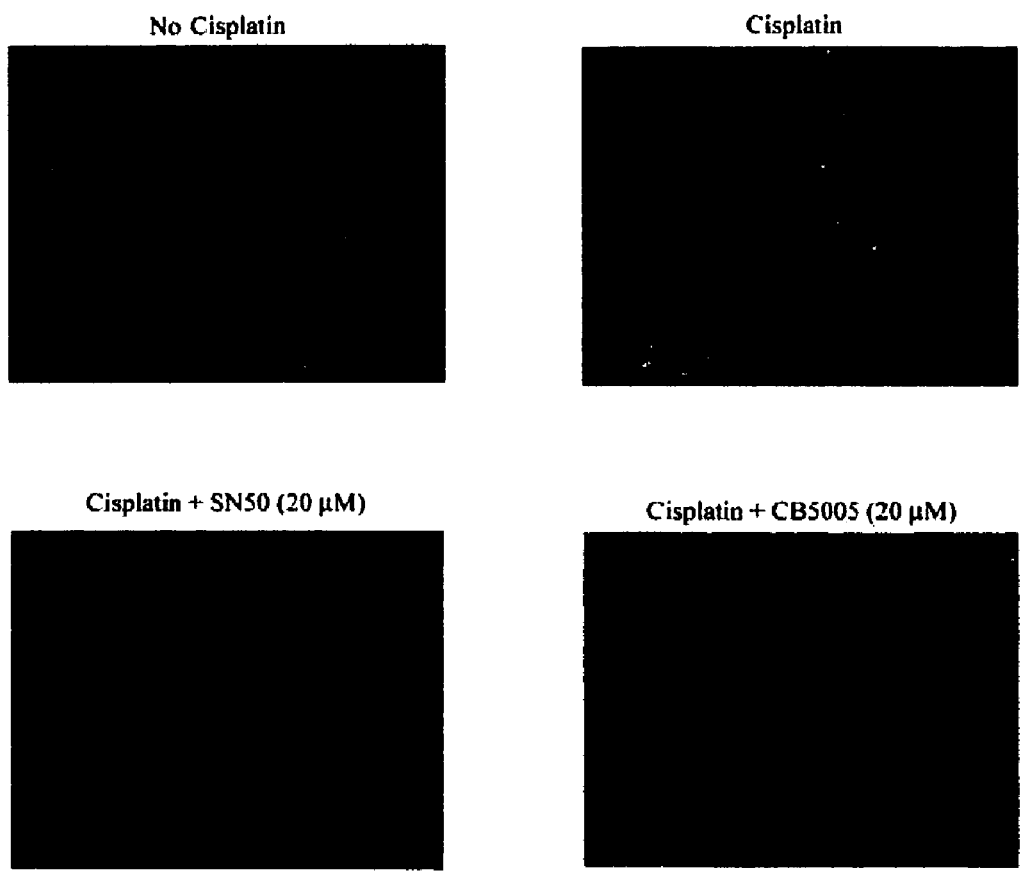
FIG. 14 illustrates apoptotic DU145 cells using the TUNEL reaction kit (Roche), which preferentially labels DNA strand breaks generated during apoptosis. DU145 cells on 8-well chamber slides were treated with CB5005 (SEQ ID NO: 4) or SN50 (a peptide comprising a signal peptide sequence and an NF-kB nuclear localization sequence, described in U.S. Pat. No. 5,807,746 to Lin, et al.) at the indicated concentrations or diluent for 30 min followed by cisplatin (5 µg/ml) or diluent for an additional 16 h. Dark brown areas indicated DNA fragmentation detected in the nuclei, a common sign of apoptosis.
Figure 15:
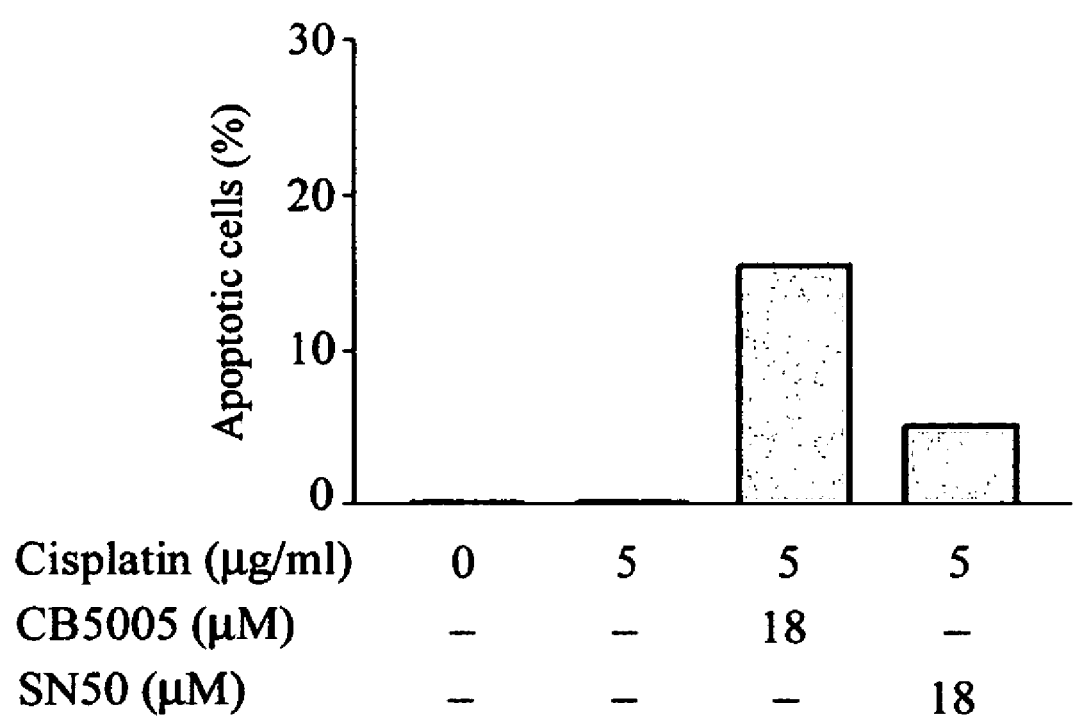
FIG. 15 indicates percentages of the apoptotic cells induced by cisplatin in the absence or presence of CB5005 (SEQ ID NO: 4) or SN50 in DU145 cells, as calculated from the results of flow cytometric analysis. DU145 cells were treated with CB5005 (SEQ ID NO: 4) (18 µM), SN50 (18 µM), or diluent for 30 min followed by cisplatin at 5 µg/ml for an additional 21 h. The cells stained with annexin V/PI were then analyzed by flow cytometry.

SN50, a commercially available 26-mer peptide used in a variety of research studies to date, has demonstrated effectiveness for inhibiting NF-κB nuclear translocation in a number of types of cells. The inventors performed side-by-side comparisons of CB5005 peptide (SEQ ID NO: 4) with SN50 peptide in apoptosis assays, such as the TUNEL assay (which preferentially labels DNA strand breaks generated during apoptosis, as shown in FIG. 14) and flow cytometry analysis (which quantitatively measures the level of annexin V/PI labeling of the apoptotic cells as shown in FIG. 15). In both, CB5005 (SEQ ID NO: 4) exhibited significantly more activity than SN50 in promoting cisplatin-induced apoptosis in androgen-insensitive PCA cells.

CB5005 (SEQ ID NO: 4) Exhibits Higher Cellular Import Activity Than SN50

Figure 16:
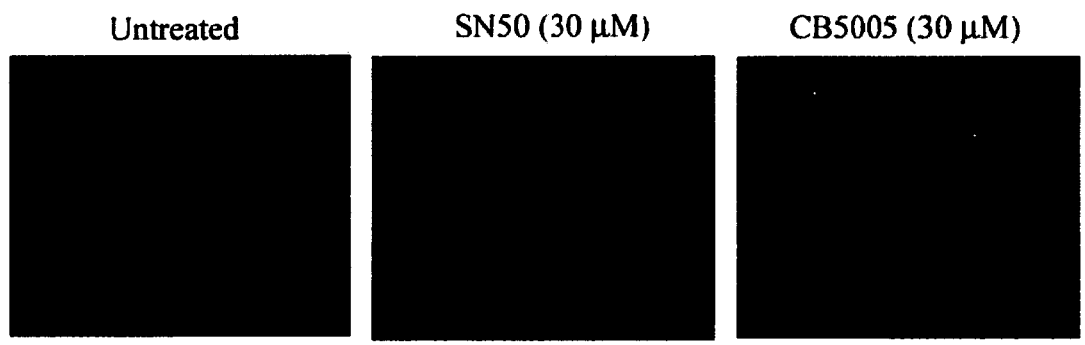
FIG. 16 illustrates and compares cellular import of CB5005 (SEQ ID NO: 4) and SN50 in DU145 cells by fluorescence microscopy analysis. DU145 cells on 8-well chamber slides were treated at 37° C. with diluent, CB5005 (SEQ ID NO: 4) or SN50 at 30 µM for 1 h. The intracellular peptides were detected as green stains by an indirect immunofluorescence assay using anti-peptide antibody and FITC-labeled anti-rabbit antibody and analyzed by fluorescent microscopy.

To determine whether the higher apoptotic activity of CB5005 peptide (SEQ ID NO: 4) in PCA cells was at least in part due to its higher cell membrane-translocating activity, the inventors performed side-by-side comparisons of CB5005 peptide (SEQ ID NO: 4) with well-known cell-permeable SN50 peptide in a cellular import study using an indirect immunofluorescence assay. As shown in FIG. 16, CB5005 (SEQ ID NO: 4) exhibited significantly higher import activity than SN50 peptide.

We claim:

1. An isolated polypeptide comprising a cell-permeable peptide of about 11 to about 50 residues comprising SEQ ID NO: 2 and an NF-kB nuclear localization sequence.

2. An isolated polypeptide as in claim 1 wherein the NF-kB nuclear localization sequence comprises NF-KB p50.

3. An isolated cell permeable peptide of about 11 to about 50 amino acids comprising SEQ ID NO: 2.

* * * * *